(12) United States Patent
Cox (10) Patent No.: US 8,241,348 B2
(45) Date of Patent: Aug. 14, 2012

(54) INTRAVASCULAR STENT FOR TREATING VULNERABLE PLAQUE AND METHOD OF USE

(75) Inventor: Daniel L. Cox, Palo Alto, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 214 days.

(21) Appl. No.: 12/728,755

(22) Filed: Mar. 22, 2010

(65) Prior Publication Data

US 2010/0174303 A1  Jul. 8, 2010

Related U.S. Application Data

(62) Division of application No. 10/280,632, filed on Oct. 25, 2002, now Pat. No. 7,731,744.

(51) Int. Cl.
*A61F 2/06* (2006.01)
(52) U.S. Cl. ........................ 623/1.32; 623/1.15
(58) Field of Classification Search ........... 606/200; 623/1.29, 1.32, 1.16, 1.14, 1.1, 1.15
See application file for complete search history.

(56) References Cited

U.S. PATENT DOCUMENTS

| | | | |
|---|---|---|---|
| 6,027,526 A | 2/2000 | Limon et al. | |
| 6,258,115 B1 * | 7/2001 | Dubrul | 606/200 |
| 6,325,826 B1 | 12/2001 | Vardi et al. | |
| 6,475,233 B2 * | 11/2002 | Trozera | 623/1.15 |
| 6,485,507 B1 * | 11/2002 | Walak et al. | 623/1.15 |
| 7,331,987 B1 | 2/2008 | Cox | |
| 2003/0065381 A1 | 4/2003 | Solar | |
| 2003/0125799 A1 | 7/2003 | Limon | |
| 2003/0171765 A1 * | 9/2003 | Kokate et al. | 606/159 |

* cited by examiner

*Primary Examiner* — Corrine M McDermott
*Assistant Examiner* — Melissa Ryckman
(74) *Attorney, Agent, or Firm* — Fulwider Patton LLP

(57) ABSTRACT

An expandable stent is implanted in a body lumen, such as a coronary artery, peripheral artery, or other body lumen for rupturing a fibrous cap to controllably release vulnerable plaque. The invention provides for a an intravascular stent having a plurality of cylindrical rings connected by links. The stent includes struts and links of varying strengths about the circumference of the stent. The weaker struts and links require less force to open and, hence, may apply more stress to rupture the fibrous cap while the stronger struts and links protect the healthy portions of the body lumen. In another embodiment, the stent may include stress concentrators positioned on outer surfaces of the links. The stress concentrators are aligned with the fibrous cap prior to stent expansion so that upon stent expansion, the stress concentrators induce stress to rupture the fibrous cap, thereby releasing the vulnerable plaque.

6 Claims, 6 Drawing Sheets

INTRAVASCULAR STENT FOR TREATING VULNERABLE PLAQUE AND METHOD OF USE

CROSS-REFERENCES TO RELATED APPLICATIONS

This is a divisional application of U.S. Ser. No. 10/280,632, filed Oct. 25, 2002, which issued as U. S. Pat. No. 7,731,744. Applicant claims priority to this application. The foregoing application is incorporated herein by reference thereto.

BACKGROUND OF THE INVENTION

This invention relates to vascular repair devices, and in particular intravascular stents, which are adapted to be implanted into a patient's body lumen, such as a blood vessel or coronary artery, to maintain the patency thereof. Stents are particularly useful in the treatment of atherosclerotic stenosis in arteries and blood vessels.

Stents are generally tubular-shaped devices which function to hold open a segment of a blood vessel or other body lumen such as a coronary artery. They also are suitable for use to support and hold back a dissected arterial lining that can occlude the fluid passageway. At present, there are numerous commercial stents being marketed throughout the world.

Balloon dilatation catheters are sometimes used to pre-dilate a diseased vessel prior to installation of a stent. Some balloon dilatation catheters include cutters, or atherotomes, which are placed longitudinally along the length of the balloon. The cutters create incisions in the vessel to provide greater control over the area of the vessel which stretches most during a balloon dilatation procedure. The incisions relieve pressure in the wall of the vessel, thereby enhancing dilation of the vessel by the balloon and allowing the vessel to be dilated more readily at a lower pressure. However, lesions are typically non-concentric, but the force from a balloon during a dilatation procedure is uniform. A nonuniform force distribution may not be desirable because the healthy portion of a vessel is typically the thinnest and weakest and consequently stretches more than the diseased portion. It is more desirable to deform the diseased portion of the vessel, such as a calcified lesion.

Further, some coronary arteries may develop vulnerable plaque which may require treatment through stenting. A vulnerable plaque is typically composed of a thin fibrous cap over a large lipid pool. It is sometimes desirable to rupture the fibrous cap during a stenting procedure and drain the lipid pool. Such a controlled rupture allows a physician to immediately respond to any complications such as a thrombus formation. What has been needed and heretofore unavailable is a stent that opens more easily in selected portions of the stent circumference compared to the remainder of the stent to increase stress on the diseased portions of the artery and reduce stress on healthy tissue. What also has been needed is a stent which induces stress to the fibrous cap which retains the vulnerable plaque during opening of the stent to cause rupture to the fibrous cap during the stenting procedure. The present invention satisfies these needs. The stent of the present invention includes portions of varying strength about its circumference. The stent also includes stress concentrators on the exterior portion of the stent. Each of these elements contribute to inducing more stress to the fibrous cap which retains vulnerable plaque and rupturing of the fibrous cap to effect a controlled release of vulnerable plaque contents during stent opening.

SUMMARY OF THE INVENTION

The present invention is directed to an intravascular stent which is configured to rupture a fibrous cap thereby controllably releasing vulnerable plaque during stent expansion and stable enough radially in its expanded condition to maintain the patency of a body lumen such as an artery when the stent is implanted therein. The novel stent pattern of the invention is particularly well suited for rupturing the fibrous cap located in, for example, the coronary arteries.

The stent of the present invention generally includes a plurality of cylindrical rings that are interconnected. The stent typically is mounted on a balloon catheter if it is balloon expandable or mounted on a catheter without a balloon if it is self expanding.

In one embodiment of the invention, the stent has a distal and proximal section formed of rings or cylindrical elements and links. The rings and links are configured so that the metallic surface area (metal-to-artery ratio) is less than 20% and preferably is between about 20% and 10%, thus providing good scaffolding and providing a more cylindrical lumen. The stent includes a first side of the circumference and a second side of the circumference with the second side being weaker than the first side. The weakness in the second side may be induced by making the struts and links on the second side smaller than the struts and links on the first side, which causes the second side to scaffold less. In use, the second side of the stent is aligned with an area of vulnerable plaque. Being weaker, the second side of the stent restrains the balloon less during stent expansion than does the first side of the stent. Therefore, the second side of the stent expands at a quicker rate than the first side and transfers more stress to the body lumen to induce extra force at the vulnerable plaque when the stent is implanted in an attempt to rupture the fibrous cap over the vulnerable plaque. Conversely, the first side of the stent protects healthy vessel tissue from expansion forces of the stent.

The cylindrical rings and links can have various configurations. In one embodiment, each of the cylindrical rings making up the stent have a proximal end and a distal end and a cylindrical plane defined by a cylindrical outer wall surface that extends circumferentially between the proximal end and the distal end of the cylindrical ring. The cylindrical rings are interconnected by at least one link which attaches one cylindrical ring to an adjacent cylindrical ring. The links are positioned substantially within the cylindrical plane of the outer wall surface of the cylindrical rings. The design of the links and their placement nested within a W-shaped member provides for uniform scaffolding and a high degree of vessel wall coverage throughout the stent.

The cylindrical rings typically are formed of a plurality of peaks and valleys, where the valleys of one cylindrical ring are circumferentially aligned with the valleys of an adjacent cylindrical ring. In this configuration, at least one link attaches each cylindrical ring to an adjacent cylindrical ring so that the links are positioned substantially within one of the valleys and attaches the valley to an adjacent valley.

While the cylindrical rings and links generally are not separate structures, they have been conveniently referred to as rings and links for ease of identification. Further, the cylindrical rings can be thought of as comprising a series of U-, W- and Y-shaped structures in a repeating pattern. Again, while the cylindrical rings are not divided up or segmented into U's, W's and Y's, the pattern of the cylindrical rings resemble such configuration. The U's, W's and Y's promote flexibility in the stent primarily by flexing and by tipping radially outwardly as the stent is delivered through a tortuous vessel.

The links are positioned to be within the curved part of the W-shaped portion which generally increases the amount of vessel wall coverage. Since the link does not expand when the stent is expanded, it will continue to provide good vessel wall coverage even as the curved part of the W-shaped portion spreads apart as the stent is expanded.

In another embodiment of the invention, the links are circumferentially aligned between adjacent cylindrical rings, thereby forming a bar between the proximal cylindrical ring and the distal cylindrical ring. Stress concentrators, such as incisors, are positioned on an outer surface of the links. During use, the stress concentrators are aligned with the vessel lesion, such as the fibrous cap. Expansion of the stent causes the stress concentrators to induce additional force against the vessel lesion for cutting the vessel lesion or causing the fibrous cap to rupture. The stress concentrators may also be aligned with healthy portions of the vessel to induce incisions therein to facilitate dilatation of the vessel.

The cylindrical rings of the stent are plastically deformed when expanded when the stent is made from a metal that is balloon expandable. Typically, the balloon expandable stent is made from a stainless steel alloy or similar material.

Similarly, the cylindrical rings of the stent expand radially outwardly when the stent is formed from a superelastic alloy, such as nickel titanium (NiTi). In the case of superelastic alloys, the stent expands upon application of a temperature change or when a stress is relieved, as in the case of a pseudoelastic phase change.

The stents of the embodiments described above may also be made of a superelastic material with the memory set in a crimped configuration, thereby making the stent self contracting. In this embodiment, the contraction forces of the stent cause the stent to hold onto the balloon. During use, the balloon is inflated and the stent expanded until the fibrous cap is ruptured, after which the balloon is deflated. During deflation of the balloon, the contraction forces of the stent help reduce the profile of the balloon as the stent and catheter assembly are withdrawn from the patient.

The number and location of links that interconnect adjacent cylindrical rings can be varied as the application requires. Since the links typically do not expand when the cylindrical rings of the stent expand radially outwardly, the links continue to provide a scaffolding function to assist in holding open the artery.

The stent may be formed from a tube by laser cutting the pattern of cylindrical rings and links in the tube. The stent also may be formed by laser cutting a flat metal sheet in the pattern of the cylindrical rings and links, and then rolling the pattern into the shape of the tubular stent and providing a longitudinal weld to form the stent.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

The present invention stent improves on existing stents by providing concentrated stress points about the circumference of the stent. The design of the stent increases pressure against diseased portions of the artery, such as vulnerable plaque, while inducing less stress against healthier portions of the artery during stent opening. The stent also facilitates rupture of the fibrous cap for controllably releasing the vulnerable plaque contents during stent opening.

Figure 1:
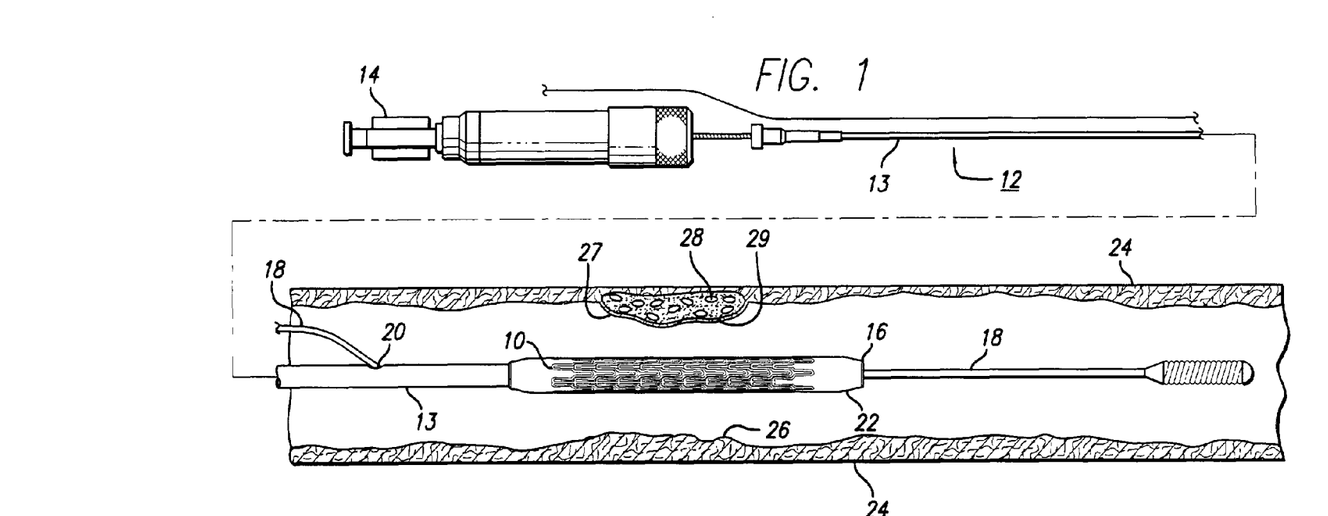
FIG. 1 is an elevational view, partially in section, of a stent embodying features of the invention and which is mounted on a rapid-exchange delivery catheter and positioned within an artery.

Turning to the drawings, FIG. 1 depicts stent 10 of the present invention mounted on a catheter assembly 12 which is used to deliver the stent and implant it in a body lumen, such as a coronary artery, peripheral artery, or other vessel or lumen within the body. The catheter assembly includes a catheter shaft 13 which has a proximal end 14 and a distal end 16. The catheter assembly is configured to advance through the patient's vascular system by advancing over a guide wire by any of the well known methods of an over the wire system (not shown) or a well known rapid exchange catheter system, such as the one shown in FIG. 1.

The catheter assembly 12, as depicted in FIG. 1, is of the well known rapid exchange (RX) type which includes an RX port 20 where the guide wire 18 will exit the catheter. The distal end of the guide wire 18 exits the catheter distal end 16 so that the catheter advances along the guide wire on a section of the catheter between the RX port 20 and the catheter distal end 16. As is known in the art, the guide wire lumen which receives the guide wire is sized for receiving various diameter guide wires to suit a particular application. The stent is mounted on the expandable member 22 (balloon) and is crimped tightly thereon so that the stent and expandable member present a low profile diameter for delivery through the arteries.

As shown in FIG. 1, a partial cross-section of an artery 24 is shown with a small amount of plaque 26 that has been previously treated by an angioplasty or other repair procedure. The stent 10 of the present invention is used to repair a diseased or damaged arterial wall which may include the plaque 26 as shown in FIG. 1, or vulnerable plaque 27 which is commonly found in the coronary arteries, peripheral arteries and other vessels. Vulnerable plaque consists of a thrombogenic lipid 28 that is covered by a thin fibrous cap 29. The stent of the invention is configured to rupture the fibrous cap covering vulnerable plaque and to drain the lipid pool, thereby repairing the vessel.

Figure 2:
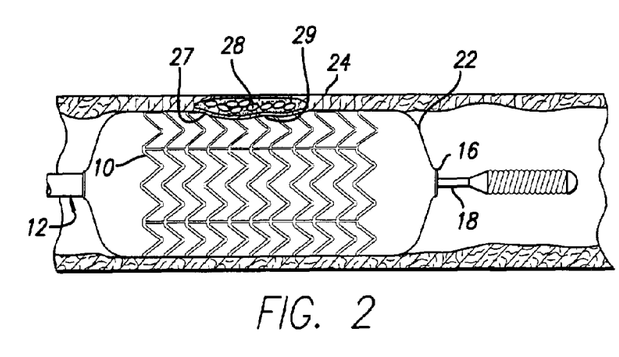
FIG. 2 is an elevational view, partially in section, similar to that shown in FIG. 1 wherein the stent is expanded within the artery, so that the stent embeds within the arterial wall.

In a typical procedure to implant the stent 10, the guide wire 18 is advanced through the patient's vascular system by well known methods so that the distal end of the guide wire is advanced past the plaque or diseased area 26. Prior to implanting the stent, the cardiologist may wish to perform an angioplasty procedure or other procedure (i.e., atherectomy) in order to open the vessel and remodel the diseased area. Thereafter, the stent delivery catheter assembly 12 is advanced over the guide wire so that the stent is positioned in the target area. The expandable member or balloon 22 is inflated by well known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, arid subsequently is withdrawn from the patient's vascular system. As depicted in FIG. 2, the balloon is fully inflated with the stent expanded and pressed against the vessel wall, and in FIG. 3, the implanted stent remains in the vessel after the balloon has been deflated and the catheter assembly and guide wire have been withdrawn from the patient. As further illustrated in FIG. 3, the stent ruptures the fibrous cap 29 covering the vulnerable plaque 27 during dilatation, thereby causing the lipid pool 28 to drain.

Figure 3:
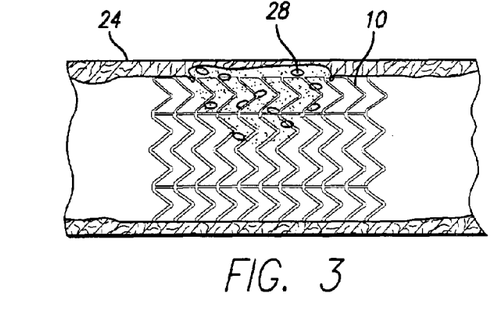
FIG. 3 is an elevational view, partially in section, showing the expanded stent implanted within the artery after withdrawal of the rapid-exchange delivery catheter and thrombogenic lipid draining from a vulnerable plaque.

Stent 10 serves to hold open the artery after the catheter is withdrawn, as illustrated by FIG. 3. Due to the formation of the stent from an elongated tubular member, the undulating components of the stent are relatively flat in transverse cross-section, so that when the stent is expanded, it is pressed into the wall of the artery and as a result does not interfere with the blood flow through the artery. The stent is pressed into the wall of the artery and will eventually be covered with smooth muscle cell growth which further minimizes blood flow interference. The undulating portion of the stent provides good tacking characteristics to prevent stent movement within the artery.

Figure 4:
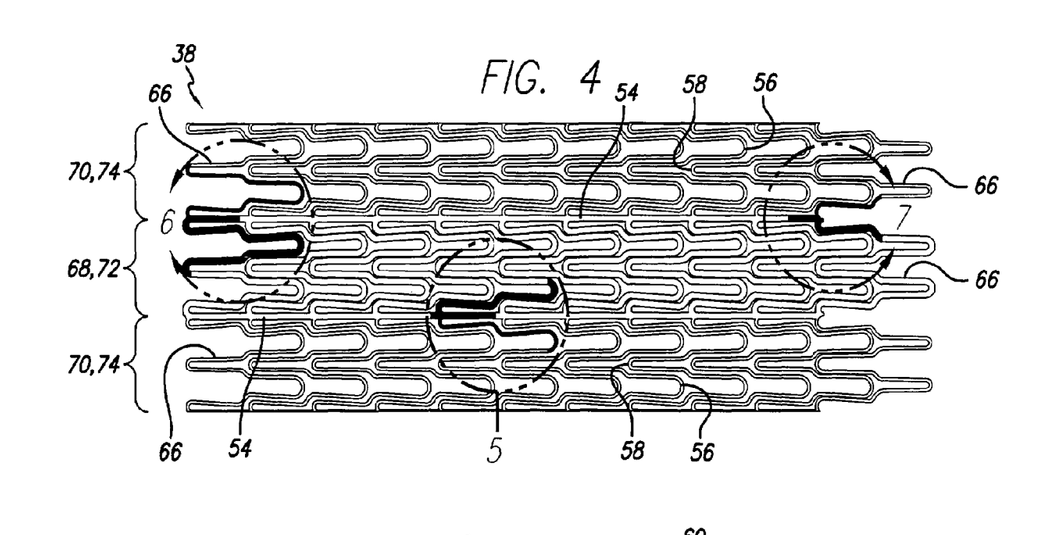
FIG. 4 is a plan view of a flattened stent of the invention which illustrates the pattern of the stent shown in FIGS. 1-3.

In keeping with the present invention, FIGS. 4-10 depict the stent 10 in various configurations. Turning to FIG. 4, stent 10 is shown in a flattened condition so that the pattern can be clearly viewed, even though the stent is never in this form unless it is formed from a flat sheet. The stent is typically formed from a tubular member, however, it can be formed from a flat sheet such as shown in FIG. 4 and rolled into a cylindrical configuration.

With respect to the structure of the cylindrical rings and links, virtually any pattern is acceptable. Typically, the rings are in the form generally of an undulating pattern 38 that can easily expand radially outwardly or compress radially inwardly. Thus, as described immediately below, an example of cylindrical rings 40 and links 54 are described, however, other patterns are envisioned that would perform equally as well in rupturing the vulnerable plaque 27 and supporting the vessel 24.

Figure 6:
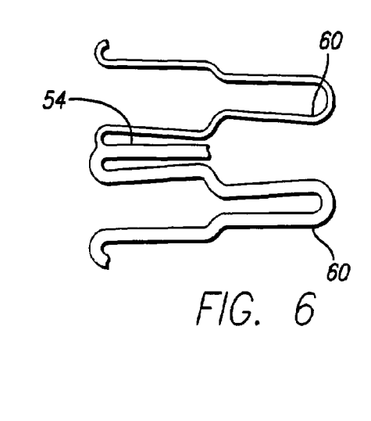
FIG. 6 is an enlarged sectional view of FIG. 4 depicting several peaks of a cylindrical ring.
Figure 7:
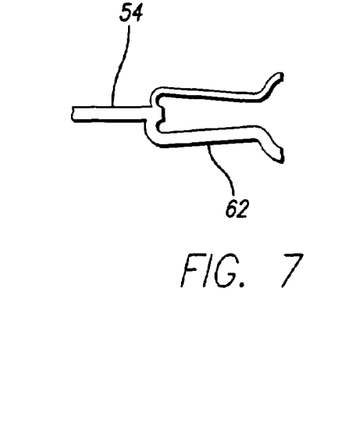
FIG. 7 is an enlarged sectional view of FIG. 4 depicting a Y-shaped portion of the cylindrical ring.
Figure 8A:
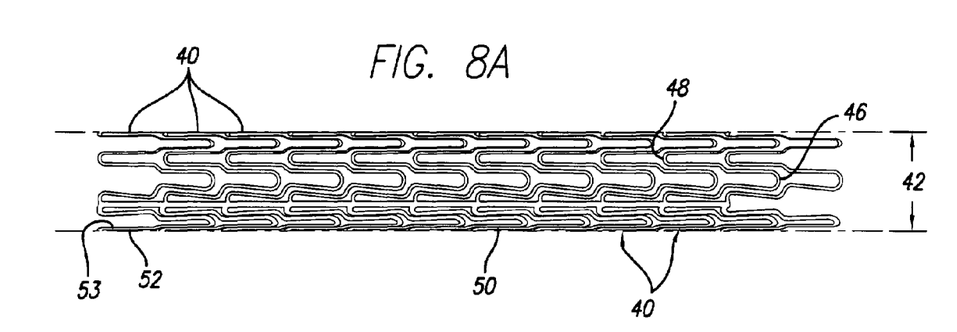
FIG. 8A is a side view of a stent embodying features of the invention in an unexpanded state.
Figure 8B:
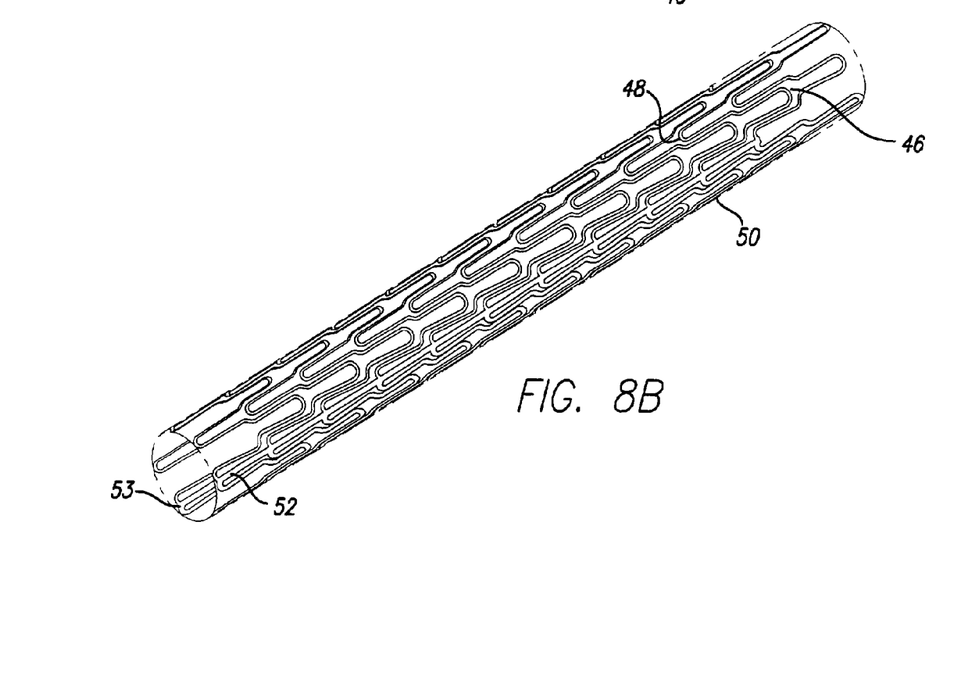
FIG. 8B is a perspective view of the stent of FIG. 8A depicting the cylindrical wall defined by each cylindrical ring.
Figure 9:
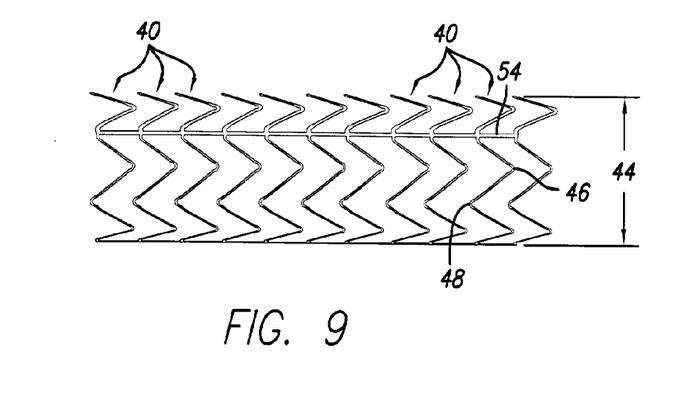
FIG. 9 is a side view of the stent of FIG. 8A in an expanded condition.
Figure 10:
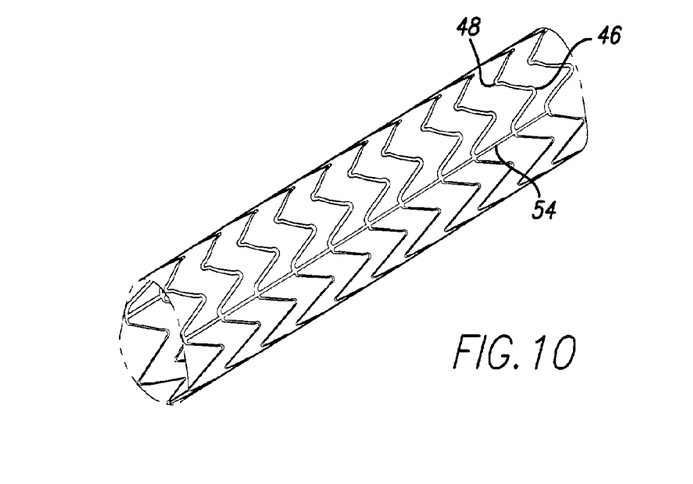
FIG. 10 is a perspective view of the stent of FIG. 8A in an unexpanded condition.
Figures 11, 12, 13:
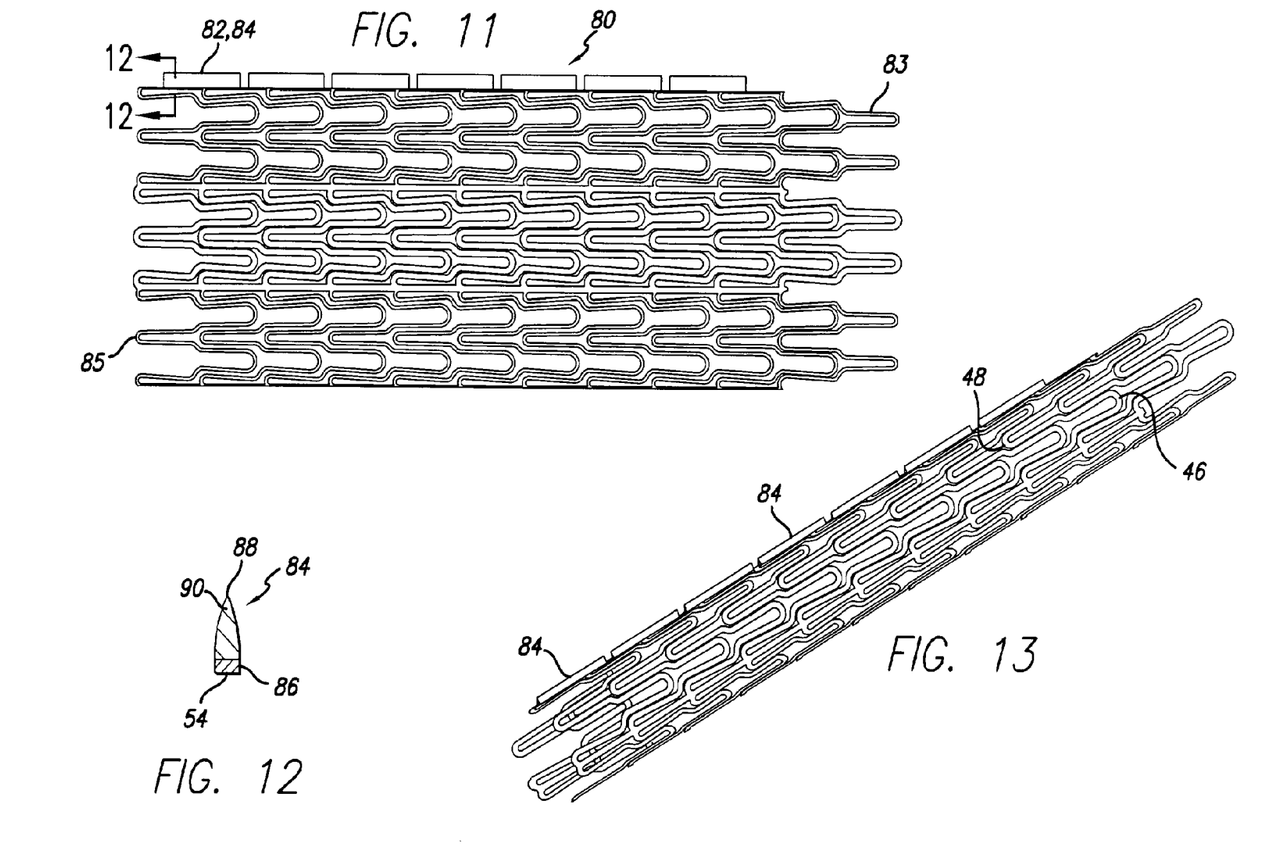
FIG. 11 is a plan view of a flattened stent of the invention including stress concentrators positioned on links.
FIG. 12 is a side view depicting a profile of the stress concentrator of FIG. 11.
FIG. 13 is a perspective view of the stent of FIG. 11 in an unexpanded state.

As shown in FIGS. 4-10, stent 10 is made up of a plurality of cylindrical rings 40 which extend circumferentially around the stent when it is in a tubular form (see FIGS. 8A and 8B). The stent has a delivery diameter 42 as shown in FIG. 8A, and an implanted diameter 44 as shown in FIG. 9. Each cylindrical ring 40 has a cylindrical ring proximal end 46 and a cylindrical ring distal end 48. Typically, since the stent is laser cut from a tube there are no discreet parts such as the described cylindrical rings. However, it is beneficial for identification and reference to various parts to refer to the cylindrical rings and the following parts of the stent.

Each cylindrical ring 40 defines a cylindrical plane 50 which is a plane defined by the proximal and distal ends 46, 48 and the circumferential extent as the cylindrical ring travels around the cylinder. Each cylindrical ring includes a cylindrical outer wall surface 52 which defines the outermost surface of the stent, and a cylindrical inner wall surface 53 which defines the innermost surface of the stent. The cylindrical plane 50 follows the cylindrical outer wall surface. In keeping with the invention, links 54 are positioned within the cylindrical plane. The links connect one cylindrical ring to an adjacent cylindrical ring.

Cylindrical rings 40 can be nested such that adjacent rings slightly overlap in the longitudinal direction so that one ring is slightly nested within the next ring and so on. The degree of nesting is dictated primarily by the length of each cylindrical ring, the number of undulations in the rings, the thickness of the struts that make up the rings, and the radius of curvature, all in conjunction with the crimped or delivery diameter of the stent. If the rings are substantially nested one within the other, it may be difficult to crimp the stent to an appropriate low profile delivery diameter without the various struts overlapping. It is also contemplated that the rings are slightly nested even after the stent is expanded, which enhances vessel wall coverage. In some circumstances, it may not be desirable to nest one ring within the other, which is also contemplated by the invention.

Referring to FIGS. 4-10, stent 10 can be described more particularly as having a plurality of peaks 56 and valleys 58. Although the stent is not divided into separate elements, for ease of discussion references to peaks and valleys is appropriate. The number of peaks and valleys, can vary in number for each ring depending upon the application. Thus, for example, if the stent is to be implanted in a coronary artery, a lesser number of peaks and valleys are required than if the stent is implanted in a peripheral artery, which generally has a larger diameter than a coronary artery. As can be seen in FIG. 4, the peaks 56 are in phase, meaning that the peaks 56 all point in the same direction and are substantially aligned along the longitudinal axis of the stent. It may be desirable under certain circumstances to position peaks 56 so that they are out of phase (not shown), that is, the peaks of one ring point in the opposite direction from the peaks of an adjacent ring (i.e., the peaks of one ring point toward the peaks of an adjacent ring). As shown in FIG. 4, the peaks are substantially circumferentially aligned. Positioning the peaks, valleys, and links in this manner, provides a longitudinally flexible stent having uniform expansion capabilities, high radial strength and sufficient wall coverage to support the vessel.

Links 54 connect adjacent rings between circumferentially aligned valleys, or alternatively between circumferentially aligned peaks, wherein the links are circumferentially aligned between adjacent rings. Alternatively, the links may connect adjacent rings between alternating valleys or peaks with the link pattern being circumferentially offset between adjacent rings (not shown). The links may be substantially straight and extend substantially parallel to the longitudinal axis of the stent. Alternatively, the links may include an undulating member (not shown) positioned between straight portions of the link.

Figure 5:
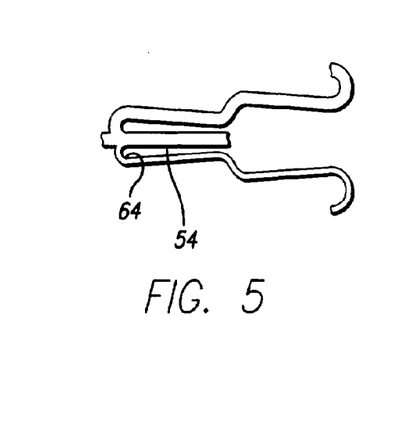
FIG. 5 is an enlarged view of a portion of the stent shown in FIG. 4 depicting a link connecting portions of adjacent cylindrical rings.

Referring to FIGS. 5-7, the stent of the invention can be described as having cylindrical rings formed of U-shaped portions 60, Y-shaped portions 62, and W-shaped portions 64. Again, while the stent is generally laser cut from a tube and it typically has no discreet parts, for ease of identification the stent of the invention also can be referred to as having U-, Y-, and W-shaped portions. The U-shaped portions have no supporting structure attached thereto. The Y-shaped portions, at their base, or apex, have the link 54 extending therefrom. The W-shaped portion has the other end of the link attached at its base or curve portion. The length of the links can vary depending upon the desired amount of separation between adjacent cylindrical rings. Preferably, the link is contained within the W-shaped portion, which should be wide enough to accommodate the link when the stent is crimped so that no portion of the link and the W-portion overlap. Preferably, the link and the W-shaped portion arc in the same cylindrical plane 50 as defined by the cylindrical outer wall surface 52 and the cylindrical inner wall surface 53.

Referring to FIG. 4, in one aspect of the invention, the stent 10 is formed so that struts 66 have variable thickness or width about the circumference of the stent. As one example, it is contemplated that the struts on a first side 68 of the circumference of the stent may be thicker or wider (larger) than the struts on the opposite, second side 70 of the circumference of the stent. The larger struts create a strong side 72 of the stent and the thinner or narrower (smaller) struts on the second side of the stent create a weak side 74 of the stent. Similarly, the links 54 on the strong side of the stent are larger than the links on the weak side of the stent. With the varying strengths between the first and second sides of the stent, the portion of the balloon 22 apposed to the weak side of the stent has a tendency to inflate at a faster rate than the portions of the balloon apposed to the strong side of the stent. Thus, more force is applied to the vessel by the weak side of the stent as opposed to the strong side of the stent. During a dilatation procedure, the weak side of the stent is aligned with the diseased portion of a vessel, such as vulnerable plaque in an artery, before expansion of the stent is commenced. The weak side of the stent expands preferentially over the strong side of the stent so that the diseased portion of the vessel is subjected to a greater load than the healthy portion of the vessel. Further, the healthy portion of the vessel is protected by the strong side of the stent. Many stent patterns may be modified to include a weak side which opens preferentially over a strong side along the circumference of the stent. Examples of such stents include multilink stents and slotted tube stents.

The stent 10 having the strong side 72 and the weak side 74 along the circumference may be part of a dilatation system which is removed after the dilatation procedure. The stent of this embodiment is made from Nitinol or other superelastic material with memory set in the crimped, delivery profile, thereby making the stent self-contracting. The stent is mounted onto a balloon 22 with the contraction forces of the stent maintaining the stent on the balloon, although the stent may additionally be bonded to the balloon. As the balloon is inflated and the stent is expanded during a dilatation procedure, the stent redistributes the expansion forces of the balloon so that there are greater stress concentrations proximate the weak side of the stent. The portion of the balloon apposed to the second side of the stent inflates preferentially over the portion of the balloon apposed to the first side of the stent. Being made from a superelastic material, the self-contracting forces of the stent aid in squeezing the balloon down to a small profile upon deflation of the balloon. The stent and catheter are then withdrawn from the patient.

Figure 14:
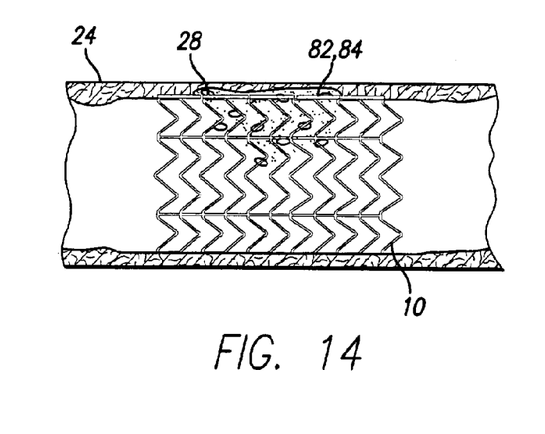
FIG. 14 is an elevational view, partially in section, showing the stent of FIG. 11 expanded and implanted within the artery after withdrawal of the rapid-exchange delivery catheter and thrombogenic lipid draining from a vulnerable plaque.

Referring to FIGS. 11-14, another embodiment of the invention includes stent 80 which may have a strut pattern similar to that of stent 10 of FIG. 4, but does not require the strong side 72 and the weak side 74. However, the stent 10 having a strong side and a weak side may be used in this embodiment. The stent 80 of this embodiment includes stress concentrators 82, such as incisors 84, positioned on the outer surfaces of links 54 to apply a substantial stress to vessel lesions, such as the fibrous cap during stent expansion. During expansion of the stent, the incisors create incisions in the vessel wall to relieve pressure in the vessel wall and to enhance dilatation. The stress concentrators also can be used for calcified or rigid plaque to open it preferentially on one side. Alternatively, the incisors are positioned next to a vulnerable plaque area prior to inflation of the balloon so that the incisors rupture the fibrous cap to controllably release the vulnerable plaque during expansion of the stent (FIG. 14). Although the stress concentrators are described herein as incisors, the stress concentrators may be in other forms, such as nodules, which may induce stress on the vessel lesions.

To reduce the tendency of the incisors 84 to scrape the vessel wall during expansion of the stent 10, the links 54 upon which the incisors are coupled are positioned parallel with the longitudinal axis of the stent to prevent circumferential movement of the links during expansion. More particularly, in one embodiment of the invention, the link pattern of the stent includes at least one series of links which has links between adjacent rings positioned in phase with the incisors positioned thereon. In this manner, each series of links forms a bar extending between a proximal ring 83 of the stent to a distal ring 85 of the stent. Preferably, the stent includes a plurality of the series of links. The incisors arc positioned aligned with the links to create a linear, longitudinal incision which is aligned with the longitudinal axis of the stent. Alternatively, the links may be positioned out of phase and the incisors positioned thereon, but the discreet, short incisions created thereby may not be as effective in enhancing dilatation of the vessel.

Although the number, size, and location of the incisors 84 depend on the stent design, a continuous incisor (not shown) along the length of stent creates a clean incision along which the artery may expand. However, an incisor which extends the length of the stent may stiffen the stent to undesirable levels. The stiffness of the stent caused by the incisors may be reduced by separating the incisor into a series of shorter segments which are aligned longitudinally with a small gap between adjacent segments to achieve a single incision along the longitudinal group of incisors. Alternatively, or in combination, the stiffness may be reduced by making the incisors from a shape memory material, such as Nitinol. In one embodiment (FIG. 12), the incisors include a spine portion 86 which is coupled to the outer surface of a link 54 and a cutting edge 88 which projects radially outward from the longitudinal axis of the stent. The sides 90 of the incisors include convex curved profiles, but may alternatively include other profiles, such as concave curved profiles or flat profiles. The height of the incisor is sufficient to create an incision in the vessel wall to facilitate dilatation of the vessel, or alternatively, to rupture the fibrous cap. In one aspect, the incisors may be positioned on only one of the series of links which is to be located over a lesion, such as a vulnerable plaque area, to avoid incising healthy vessel tissue. In another aspect, the incisors may be positioned on a plurality of the series of links.

To protect the vessel walls until the stent is positioned for deployment, a sheath or other protective covering may be used to cover the stent during delivery to the lesion.

The stent 10 having the stress concentrators 82 may be part of a dilatation system which is removed after the procedure. The stent of this embodiment is made from Nitinol or other superelastic material with memory set in the crimped, delivery profile, thereby making the stent self-contracting. The stent is mounted onto a balloon 22 with the contraction forces of the stent maintaining the stent on the balloon, although the stent may additionally be bonded to the balloon. As the balloon is inflated and the stent is expanded during a dilatation procedure, the stress concentrators cause incisions within the vessel to enhance the dilatation of the vessel. Alternatively, with the stress concentrators positioned within the vulnerable plaque area, the stress concentrators rupture the fibrous cap thereby releasing the vulnerable plaque during the dilatation procedure. Being made from a superelastic material, the self-contracting forces of the stent aid in squeezing the balloon down to a small profile upon deflation of the balloon so that the stent and balloon catheter assembly can be withdrawn from the patient.

Any portion of the disclosed stent can be made from a metal alloy or from a polymer. For example, the cylindrical rings can be made from a metal alloy while the connecting links can be made from a metal alloy or a polymer. Typically, if the links are made from a polymer, the stent will be more longitudinally flexible than if the links were made from a metal alloy. Also, the stress concentrators can be made from either a metal alloy or a polymer.

Exemplary of the metallic material used in forming the cylindrical rings, links and stress concentrators of the stent is stainless steel, titanium, nickel-titanium, tantalum, gold, cobalt-chromium, platinum, palladium, and iradium. Other metals, metal alloys and polymers may also be used to form the present invention stent.

Exemplary of the biocompatible polymer material used in forming the rings, the links or the stress concentrators includes the group of polymers consisting of polyurethanes, polyetherurethanes, polyesterurethanes, silicone, thermoplastic elastomer (C-flex), polyether-amide thermoplastic elastomer (Pebax), fluoroelastomers, fluorosilicone elastomer, styrene-butadiene rubber, butadiene-styrene rubber, polyisoprene, neoprene (polychloroprene), ethylene-propylene elastomer, chlorosulfonated polyethylene elastomer, butyl rubber, polysulfide elastomer, polyacrylate elastomer, nitrile rubber, a family of elastomers composed of styrene, ethylene, propylene, aliphatic polycarbonate polyurethane, polymers augmented with antioxidants, polymers augmented with image enhancing materials, polymers having a proton (HI) core, polymers augmented with protons (H+), butadiene and isoprene (Kraton) and polyester thermoplastic elastomer (Hytrel), polyethylene, PLA, PGA, and PLGA.

Figure 15:
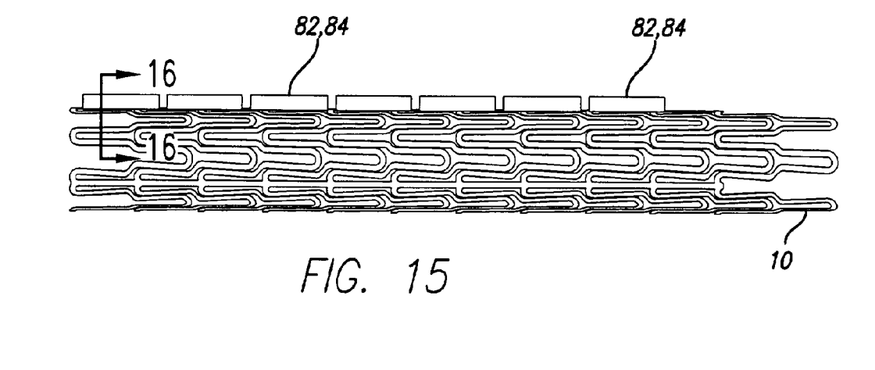
FIG. 15 is a side view of a flattened stent having a stress concentrator on selected portions.
Figure 16:
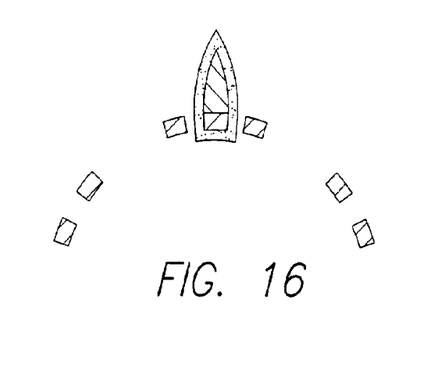
FIG. 16 is a cross-sectional view taken along lines 16-16 in FIG. 15 depicting the stress concentrator on a portion of the stent.

Stent 10 may also be used in connection with a therapeutic agent to perform a variety of functions, from preventing blood clots to promoting healing. As an example and as shown in FIGS. 15 and 16, an active agent coating 92 on the cylindrical rings, links and/or stress concentrators can inhibit the activity of endothelial cells. Similarly, an active agent coating on selective cylindrical rings 40, links and/or stress concentrators can also inhibit the activity of smooth muscle cells. More specifically, the active agent is aimed at inhibiting abnormal or inappropriate migration and proliferation of smooth muscle cells. The active agent can also include any substance capable of exerting a therapeutic or prophylactic effect in the practice of the present invention. The agent can also be for enhancing wound healing in a vascular site or improving the structural and elastic properties of the vascular site. The dosage or concentration of the active agent required to produce a favorable therapeutic effect should be less than the level at which the active agent produces toxic effects and greater than the level at which non-therapeutic results are obtained. The dosage or concentration of the active agent required to inhibit the desired cellular activity of the vascular region can depend upon factors such as the particular circumstances of the patient; the nature of the trauma; the nature of the therapy desired; the time over which the ingredient administered resides at the vascular site; and if other therapeutic agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

One particularly useful therapeutic agent for coating the stent of the invention is everolimus (available from Norvatis Pharma AG) which is a drug in the same family as rapamycin. Other examples of therapeutic agents include rapamycin, actinomycin D (ActD), or derivatives and analogs thereof ActD is manufactured by Sigma-Aldrich, 1001 West Saint Paul Avenue, Milwaukee Wis. 53233, or COSMEGEN, available from Merck. Synonyms of actinopmycin D include dactinomycin, actinomycin IV, actinomycin 11, actinomycin X1, and actinomycin C1. Examples of agents include other antiproliferative substances as well as antineoplastic, antiinflammatory, antiplatelet, anticoagulant, antifibrin, antithomobin, antimitotic, antibiotic, and antioxidant substances. Examples of antineoplastics include taxol (paclitaxel and docetaxel). Examples of antiplatelets, anticoagulants, antifibrins, and antithrombins include sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein, 11b/111a platelet membrane receptor antagonist, recombinant hirudin, thrombin inhibitor (available from Biogen), and 7E-3B® (an antiplatelet drug from Centocore). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen), angiotensin converting enzyme inhibitors such as Captopril (available from Squibb), Cilazapril (available from Hoffman-LaRoche), or Lisinopril (available from Merck); calcium channel blockers (such as Nifedipine), colchicine fibroblast growth factor (FGF) antagonists, fish oil (omega 3-fatty acid), histamine antagonist, Lovastatin (an inhibitor of HMG-CoA reductase, a cholesterol lowering drug from Merck), monoclonal antibodies (such as PDGF receptors), nitroprusside, phosphodiesterase inhibitors, prostaglandin inhibitor (available from Glazo), Seramin (a PDGF antagonist), serotonin blockers, steroids, thioprotease inhibitors, triazolopyrimidine (a PDGF antagonist), and nitric oxide. Other therapeutic substances or agents which may be appropriate include alpha-interferon, genetically engineered epithelial cells, and dexamethasone.

The stent 10 of the present invention can be made in many ways. One method of making the stent is to cut a thin-walled tubular member, such as stainless steel tubing to remove portions of the tubing in the desired pattern for the stent, leaving relatively untouched the portions of the metallic tubing which are to form the stent. In accordance with the invention, it is preferred to cut the tubing in the desired pattern by means of a machine-controlled laser as is well known in the art.

After laser cutting the stent pattern the stents are preferably electrochemically polished in an acidic aqueous solution such as a solution of ELECTRO-GLO#300, sold by ELECTRO-GLO Co., Inc. in Chicago, Ill., which is a mixture of sulfuric acid, carboxylic acids, phosphates, corrosion inhibitors and a biodegradable surface active agent. Other electropolishing solutions are well known in the art. The stents may be further treated if desired, for example by applying a biocompatible coating such as described above.

Other methods of forming the stent of the present invention can be used, such as chemical etching; electric discharge machining; laser cutting a flat sheet and rolling it into a cylinder; and the like, all of which are well known in the art at this time.

The stent of the present invention also can be made from metal alloys other than stainless steel, such as shape memory alloys. Shape memory alloys are well known and include, but are not limited to, nickel-titanium and nickel/titanium/vanadium. Any of the shape memory alloys can be formed into a tube and laser cut in order to form the pattern of the stent of the present invention. As is well known, the shape memory alloys of the stent of the present invention can include the type known as thermoelastic martensitic transformation, or display stress-induced martensite. These types of alloys are well known in the art and need not be further described here.

The stress concentrators may be made of the same materials as the stent, such as stainless steel or shape memory alloys. In one embodiment, the stress concentrators and the stent may be made from the same piece of material. In other embodiments, the stress concentrators are coupled to the stent, such as by adhesive bonding, laser bonding or fusion, or other methods well known in the art. In embodiments wherein the stress concentrators are coupled to the stent, the stress concentrators and the stent may be made from different materials.

Importantly, a stent formed of shape memory alloys, whether the thermoelastic or the stress-induced martensite-type, can be delivered using a balloon catheter of the type described herein, or in the case of stress induced martensite, be delivered via a catheter without a balloon or a sheath catheter.

While the invention has been illustrated and described herein, in terms of its use as an intravascular stent, it will be apparent to those skilled in the art that the stent can be used in other body lumens. Further, particular sizes and dimensions, number of peaks per ring, materials used, and the like have been described herein and are provided as examples only. Other modifications and improvements may be made without departing from the scope of the invention.

What is claimed:

1. A method of rupturing a fibrous cap for controllably releasing vulnerable plaque in a body lumen, comprising:
   providing a catheter assembly having a catheter shaft having a proximal end, a distal end and an expandable member positioned at the distal end of the catheter shaft;
   an intravascular stent having a plurality of cylindrical rings, each ring having a strut pattern and being aligned along a common longitudinal axis of the stent and defining a stent circumference;
   a plurality of links interconnecting adjacent cylindrical rings;
   a first side of the circumference of the stent;
   a second side of the circumference of the stent;
   wherein the struts and links of the first side of the stent are relatively stronger than the struts and links of the second side of the stent;
   providing a guide wire having a proximal end and a distal end;
   advancing the guide wire through the body lumen until the distal end of the guide wire is distal to the fibrous cap;
   advancing the catheter assembly over the guide wire until the stent is positioned in a target area including the fibrous cap
   aligning the second side of the stent with the fibrous cap;
   inflating the expandable member to expand the stent until the stent is apposed to a wall of the body lumen and the fibrous cap ruptures thereby controllably releasing the vulnerable plaque;
   deflating the expandable member;
   removing the catheter assembly from the body lumen; and
   removing the guide wire from the body lumen.

2. The method of claim 1, wherein:
   providing a catheter assembly includes providing a stent having a delivery diameter;
   inflating the expandable member expands the stent to an implanted diameter thereby implanting the stent in the wall of the body lumen;
   deflating the expandable member separates the expandable member from the stent leaving the stent implanted in the wall of the body lumen at the target area; and
   removing the catheter assembly from the body lumen includes removing the catheter shaft and expandable member leaving the stent permanently implanted in the wall of the body lumen at the target area.

3. The method of claim 1, wherein:
   providing a catheter assembly includes providing a stent which is self-contracting and having a delivery diameter;
   inflating the expandable member expands the stent to an implanted diameter in which the stent is implanted in the wall of the body lumen;
   deflating the expandable member allows the stent to contract toward the delivery diameter; and
   removing the catheter assembly from the body lumen includes removing the catheter shaft, the expandable member and the stent.

4. A method of rupturing a fibrous cap for controllably releasing vulnerable plaque in a body lumen, comprising:
   a. providing a catheter assembly, comprising:
      a catheter having a proximal end, a distal end, a guide wire lumen and an inflation lumen;
   b. providing an intravascular stent, comprising:
      a plurality of cylindrical rings, each ring having a strut pattern and being aligned along a common longitudinal axis forming the stent;
      a plurality of a series of links, each series of links having a plurality of circumferentially aligned links interconnecting adjacent cylindrical rings, the links being straight and parallel to the longitudinal axis of the stent;
      at least one series of longitudinally aligned stress concentrator segments positioned on an outer surface of at least one of the series of links and aligned with the links, adjacent stress concentrator segments being separated by a gap; and
   c. providing an expandable member positioned at the distal end of the catheter, wherein the stent is mounted onto the expandable member;
   d. providing a guide wire having a proximal end and a distal end;

e. advancing the guide wire through the body lumen until the distal end of the guide wire is distal to the vulnerable plaque;
f. advancing the catheter assembly along the guide wire until the stent is positioned in a target area including the fibrous cap;
g. aligning one of the at least one series of stress concentrators with the fibrous cap;
h. inflating the expandable member to expand the stent until the stent is apposed to a wall of the body lumen and the series of stress concentrators, which are aligned with the fibrous cap, ruptures the fibrous cap;
i. deflating the expandable member;
j. removing the catheter assembly from the body lumen; and
k. removing the guide wire from the body lumen.

5. The method of claim 4, wherein:
providing a catheter assembly includes providing a stent having a delivery diameter;
inflating the expandable member expands the stent to an implanted diameter wherein the stent is implanted in the wall of the body lumen;
deflating the expandable member separates the expandable member from the stent while the stent remains implanted in the wall of the body lumen at the target area; and
removing the catheter assembly from the body lumen includes removing the catheter and expandable member while the stent remains implanted in the wall of the body lumen at the target area.

6. The method of claim 4, wherein:
providing a catheter assembly includes providing a stent which is self-contracting and having a delivery diameter;
inflating the expandable member expands the stent to an enlarged diameter wherein the stent is apposed to the body lumen;
deflating the expandable member allows the stent to contract toward the delivery diameter; and
removing the catheter assembly from the body lumen includes removing the catheter, the expandable member and the stent.

* * * * *